United States Patent
Oda et al.

(10) Patent No.: US 9,873,654 B2
(45) Date of Patent: Jan. 23, 2018

(54) MIXTURE OF POLYFLUOROALKENE CARBOXYLIC ACIDS OR SALTS THEREOF AND PROCESS FOR PRODUCING THE SAME

(71) Applicant: UNIMATEC CO., LTD., Tokyo (JP)

(72) Inventors: Yuichiro Oda, Ibaraki (JP); Ryota Negishi, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 15/329,192

(22) PCT Filed: Jul. 28, 2015

(86) PCT No.: PCT/JP2015/071338
§ 371 (c)(1),
(2) Date: Jan. 25, 2017

(87) PCT Pub. No.: WO2016/021441
PCT Pub. Date: Feb. 11, 2016

(65) Prior Publication Data
US 2017/0226039 A1    Aug. 10, 2017

(30) Foreign Application Priority Data
Aug. 8, 2014   (JP) .................................. 2014-162244

(51) Int. Cl.
*C07C 51/377*    (2006.01)
*C07C 57/52*    (2006.01)

(52) U.S. Cl.
CPC ............ *C07C 51/377* (2013.01); *C07C 57/52* (2013.01)

(58) Field of Classification Search
CPC ...... C07C 51/41; C07C 51/412; C07C 51/377
See application file for complete search history.

(56) References Cited

U.S. PATENT DOCUMENTS

| | | | |
|---|---|---|---|
| 4,792,620 A * | 12/1988 | Paulik | B01J 31/0231 560/232 |
| 4,927,962 A | 5/1990 | Aramaki et al. | |
| 5,004,567 A | 4/1991 | Takahashi et al. | |
| 8,148,573 B2 * | 4/2012 | Murai | C07C 51/04 562/552 |
| 2004/0024243 A1 | 2/2004 | Mathieu et al. | |
| 2010/0288971 A1 | 11/2010 | Murata et al. | |
| 2011/0251427 A1 | 10/2011 | Murai et al. | |
| 2012/0059187 A1 | 3/2012 | Ishii et al. | |

FOREIGN PATENT DOCUMENTS

| | | |
|---|---|---|
| JP | 56-118038 | 9/1981 |
| JP | 60-123442 | 7/1985 |
| JP | 61-271245 | 12/1986 |
| JP | 62-158238 | 7/1987 |
| JP | 64-61443 | 3/1989 |
| JP | 01-153654 | 6/1989 |
| JP | 2004-505939 A | 2/2004 |
| JP | WO 2008/026393 A1 | 3/2008 |
| JP | 2009-173576 A | 8/2009 |
| JP | 2011-1340 A | 1/2011 |

OTHER PUBLICATIONS

Norskov et al, Nature Chemistry, Towards the Computational Design of Solid Catalysts, 2009, 1, pp. 37-46.*
Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.*
International Search Report from corresponding PCT application No. PCT/JP2015/071338 dated Oct. 27, 2015 (4 pgs).
International Preliminary Report on Patentability and Written Opinion from corresponding PCT application No. PCT/JP2015/071338 dated Feb. 14, 2017 (8 pgs).

* cited by examiner

*Primary Examiner* — Paul A Zucker
(74) *Attorney, Agent, or Firm* — Brinks Gilson & Lione

(57) ABSTRACT

A mixture of polyfluoroalkene carboxylic acids or salts thereof represented by the general formulas:

$$C_nF_{2n+1}CH=CF(CF_2CF_2)_mCF_2COOM$$

and $$C_{n-1}F_{2n-1}CF=CHCF_2(CF_2CF_2)_mCF_2COOM$$

wherein M is a hydrogen atom, an ammonium salt, an organic amine salt or an alkali metal, n is an integer of 1 to 6 and m is an integer of 0 to 2. The mixture of polyfluoroalkene carboxylic acids or salts thereof is produced by subjecting a polyfluoroalkane carboxylic acids represented by the general formula:

$$C_nF_{2n+1}(CH_2CF_2)(CF_2CF_2)_mCF_2COOH$$

to a dehydrofluorination reaction in the presence of a nitrogen-containing heterocyclic compound catalyst, and has a lower critical micelle concentration and less surface tension at that time, therefore, the mixture of polyfluoroalkene carboxylic acids or salts thereof can be effectively used as a surfactant in the polymerization of fluorine-containing monomers.

5 Claims, No Drawings

MIXTURE OF POLYFLUOROALKENE CARBOXYLIC ACIDS OR SALTS THEREOF AND PROCESS FOR PRODUCING THE SAME

RELATED APPLICATION

This application is a 35 U.S.C. § 371 national phase filing of International Patent Application No. PCT/JP2015/071338, filed Jul. 28, 2015, which claims priority under 35 U.S.C. § 119 to Japanese Patent Application No. 2014-162244, filed Aug. 8, 2014, the entire disclosure of which is hereby expressly incorporated by reference.

TECHNICAL FIELD

The present invention relates to a mixture of polyfluoroalkene carboxylic acids or salts thereof and a process for producing the same, and more particularly to a mixture of polyfluoroalkene carboxylic acids or salts thereof for use as an effective surfactant at the time of polymerization reaction of fluorine-containing monomers, etc. and a process for producing the same.

BACKGROUND ART

Fluorine-containing surfactants represented by the general formula RfCOOM (Rf: a perfluoroalkyl group, and M: an alkali metal, an ammonium group, an organic amine salt or a hydrogen atom) have been so far widely used in the emulsion polymerization of fluorine-containing monomers. Perfluorooctanoic acid (salts) $C_7F_{15}COOM$, which is one of them and a typical example, is well known as the most distinguished surfactant, because of its good monomer emulsificability and latex stability, and easy washability following the salting-out operation.

However, it is reported that compounds containing a perfluoroalkyl group having 7 or more carbon atoms are biologically degraded in the environment and converted to those having relatively high bioaccumulation and environmental condensation, causing concerns for exposure during treatment processes, and for release or diffusion from waste, treated substrates, etc., into the environment.

In contrast, compounds containing a perfluoroalkyl group having 6 or less carbon atoms have low persistence in the environment or the human body; however, their critical micelle concentration [CMC] is high, and desired sufficient emulsification performance cannot be thus obtained.

A possible means for imparting environmental degradability is that a hydrogenated part is formed in the perfluorinated hydrophobic group in a fluorine-containing surfactant compound. Further, as a means for weakening the environmental persistence of decomposed products, it is considered desirable that the hydrophobic group has 6 or less of continuous perfluorinated-carbon atoms, such as $RfC_nH_{2n}C_mF_{2m}$- (Rf: a $C_1$-$C_6$ perfluoroalkyl group, n: an integer of 1 or more and m: an integer of 1 to 6).

The present applicant has previously reported that a polyfluoroalkane carboxylic acids (salts) represented by the general formula $C_nF_{2n+1}(CH_2CF_2)_m(CF_2CF_2)_{1-1}CF_2COOM$ (M: H, an $NH_4$ group or an alkali metal, n: 1 to 6, m: 1 to 4 and 1:1 or 2) effectively serves as a surfactant having excellent monomer emulsifiability and latex stability when used as an emulsifying agent or a dispersing agent in the polymerization reaction of fluorine-containing monomers, and that the polyfluoroalkane carboxylic acids (salts) effectively serves as a surfactant that can increase the micellar dissolution of fluorine-containing monomers, such as vinylidene fluoride, when used as an emulsifying agent or a dispersing agent in the homopolymerization or copolymerization reaction of vinylidene fluoride (Patent Document 1).

Patent Document 1 indicates that the amount of vinylidene fluoride dissolved in an aqueous polyfluoroalkane carboxylic acid ammonium solution is larger than the amount of vinylidene fluoride dissolved in an aqueous perfluorooctanoic acid ammonium solution at the same temperature and the same pressure; however, the critical micelle concentration and the surface tension at that time are nowhere described.

PRIOR ART DOCUMENTS

Patent Documents

Patent Document 1: WO2008/026393A1
Patent Document 2: JP-A-2009-173576

OUTLINE OF THE INVENTION

Problem to be Solved by the Invention

An object of the present invention is to provide a mixture of polyfluoroalkene carboxylic acids (salts) that have a low critical micelle concentration and less surface tension at that time, and that can be effectively used as, for example, a surfactant in the polymerization of fluorine-containing monomers; and a process for producing the same.

Means for Solving the Problem

The above object of the present invention can be achieved by a mixture of polyfluoroalkene carboxylic acids or salts thereof represented by the general formulas:

and

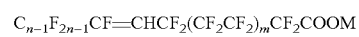

wherein M is a hydrogen atom, an ammonium salt, an organic amine salt or an alkali metal, n is an integer of 1 to 6 and m is an integer of 0 to 2.

The mixture of polyfluoroalkene carboxylic acids is produced by subjecting a polyfluoroalkane carboxylic acid represented by the general formula:

wherein n is an integer of 1 to 6 and m is an integer of 0 to 2, to a dehydrofluorination reaction in the presence of a nitrogen-containing heterocyclic compound catalyst.

Effect of the Invention

The mixture of polyfluoroalkene carboxylic acids (salts) according to the present invention comprises a terminal group having perfluoroalkyl group having 1 to 6 carbon atoms, so not only its decomposates can be kept to remain much less in the environments, but also the presence of unfluorinated hydrocarbon (—CH═) sequence can help to produce decomposates of shorter chain length than that of perfluorooctanoic acids (salts), when decomposed in the environment or metabolized in the human bodies, and thus can be used as a fluorine-containing surfactant having a low retainability in the environments or human bodies. That is, the carboxylic acids (salts) mixture has a CH═CF group that is susceptible to biological degradation (biochemical degradation by microorganisms) or chemical degradation (degradation by acid, base, active oxygen, ozone, etc., in the environment).

Furthermore, the polyfluoroalkene carboxylic acids (salts) mixture has a lower critical micelle concentration and less surface tension at that time, compared with perfluorooctanoic acid (salts); therefore, the polyfluoroalkene carboxylic acids (salts) mixture can be effectively used as a surfactant in the polymerization of fluorine-containing monomers.

EMBODIMENTS FOR CARRYING OUT THE INVENTION

The polyfluoroalkene carboxylic acids (salts) mixture is produced by subjecting the polyfluoroalkane carboxylic acids disclosed in Patent Document 1, which is represented by the formula:

$$C_nF_{2n+1}(CH_2CF_2)(CF_2CF_2)_mCF_2COOH$$

n: 1 to 6
m: 0 to 2 to a dehydrofluorination reaction in the presence of a nitrogen-containing heterocyclic compound catalyst, such as 1,8-diazabicyclo[5.4.0]undec-7-ene [DBU] or 1,5-diazabicyclo[4.3.0]non-5-ene [DBN]. These salts are produced as an ammonium salt, an organic amine salt or an alkali metal salt by a standard method in which free carboxylic acid is reacted with an ammonia, an organic amine or an alkali metal hydroxide.

This reaction smoothly proceeds only in the presence of a nitrogen-containing heterocyclic compound catalyst. If a tertiary amine, such as triethylamine, is used in place of the nitrogen-containing heterocyclic compound catalyst, the dehydrofluorination reaction does not proceed. Moreover, if the reaction is performed using KOH, as described in Patent Document 2, as a catalyst in place of the nitrogen-containing heterocyclic compound, complicated side reactions occur in the terminal carboxylic acid moiety, and the desired dehydrofluorination product cannot be obtained. The nitrogen-containing heterocyclic compound is generally used at a ratio of 1 to 5 moles, preferably 1.5 to slightly over 2.5 moles, per mole of the raw material polyfluoroalkane carboxylic acid. The dehydrofluorination reaction is performed at room temperature.

The dehydrofluorination reaction product comprises a mixture of $$C_nF_{2n+1}CH=CF(CF_2CF_2)_mCF_2COOH$$

and $$C_{n-1}F_{2n-1}CF=CHCF_2(CF_2CF_2)_mCF_2COOH$$

$$[C_{n-1}F_{2n-1}CF=CH(CF_2CF_2)_{m+1}COOH].$$

Here, the reason that polyfluoroalkene carboxylic acids are formed as a mixture is because in the dehydrofluorination reaction, the abstraction of the H atom of the methylene chain $CH_2$ and the F atom of either one of the fluoromethylene groups $CF_2$ linking back and forth to the H atom occurs equally in the anterior-posterior position. Since it is a mixture of extremely similar structural isomers, they cannot be separated from each other; however, they have equivalent reactivity, and thus, the mixture can be directly used as a raw material for the synthesis of other substances.

The mixture of polyfluoroalkene carboxylic acid salts according to the present invention can be used as a suitable emulsifying agent for the emulsion polymerization reaction of fluorine-containing monomers, or as a suitable emulsifying agent or dispersing agent for the suspension polymerization reaction thereof. The fluorine-containing monomers for the emulsion polymerization or suspension polymerization in the presence of the surfactant include, for example, vinylidene fluoride, tetrafluoroethylene, hexafluoropropylene, chlorotrifluoroethyl ene, trifluoroethyl ene, vinyl fluoride, perfluoro(alkyl vinyl ether) having an alkyl group having 1 to 3 carbon atoms, etc. One or two or more kinds of these fluorine-containing monomers can be used in the polymerization reaction to form homopolymers or copolymers. The fluorine-containing monomers can be used to form copolymers with fluorine-free monomers, for example, propylene, ethylene, etc.

In the polymerization reaction, the surfactant can be used as an emulsifying agent for the emulsion polymerization reaction, or as an emulsifying agent or a dispersing agent for the suspension polymerization, in a proportion of about 0.05 to 5% by weight, preferably about 0.2 to 1% by weight, on the basis of water or an aqueous medium containing water-soluble alcohol, etc. The polymerization reaction can be carried out preferably in the presence of a water-soluble polymerization initiator, or a redox-based polymerization initiator formed therewith. The resulting reaction mixture can be coagulated with an aqueous solution of metal salt, followed by water washing and drying to obtain desired homopolymers or copolymers of fluorine-containing monomers.

EXAMPLES

The following describes the present invention with reference to Examples.

Reference Example 1 (Synthesis Example of a Raw Material Substance)

600 g of $CF_3(CF_2)_3(CH_2CF_2)I$ [$C_6F_{11}H_2I$] (purity: 99.5%) was charged into an autoclave having a capacity of 1,200 ml, and heated to an inside temperature of 50° C. Then, 1.35 g of a peroxide-based initiator (Percadox 16, a product of Kayaku-Akuzo Co.) dissolved in 300 g of $C_6F_{11}H_2I$ was added thereto. When the inside temperature reached 55° C., tetrafluoroethylene was portionwise-added thereto, while keeping the pressure at 0.2-0.3 MPa. When the portionwise-addition amount reached to 150 g, aging was carried out at 55°-74° C. for one hour to complete the reaction. After the completion of the reaction, cooling was conducted to recover 1010 g of a product as a mixture.

Analytical results of the obtained product by gas chromatography (GC) are given in the following Table as GC % of a compound represented by the following general formula having various values of n and 1, where the remaining 1.7GC % shows impurities of unidentified structures:

$$C_nF_{2n+1}(CH_2CF_2)(CF_2CF_2)_lI$$

TABLE

| n | l | Raw material | Product |
|---|---|---|---|
| 4 | 0 | 99.5 | 44.7 |
| 4 | 1 | | 37.1 |
| 4 | 2 | | 12.0 |
| 4 | 3 | | 3.5 |

TABLE-continued

| n | l | Raw material | Product |
|---|---|---|---|
| 4 | 4 |  | 0.8 |
| 4 | 5 |  | 0.2 |

Among the afore-mentioned reaction mixture (product), a compound (n=4 and l=2) was isolated by distillation (boiling point 85° C./3 kPa) therefrom and used as a raw material substance in Reference Example 2.

Reference Example 2

94.4 g of $CF_3(CF_2)_3(CH_2CF_2)(CF_2CF_2)_2I$ (purity: 97.0%) melted in an oven at 60° C. was charged in a glass reactor having a capacity of 500 ml, and stirred at 50° C. Then, 170.0 g of 60% fuming sulfuric acid ($SO_3$ equivalent ratio relative to raw material compound: 8.4) was added dropwise from a dropping funnel, and the mixture was then heated to 60° C. and reacted for about 69 hours. After completion of the reaction, the reaction mixture was cooled and left to stand to separate an organic phase containing carboxylic acid fluoride as the major portion from an inorganic phase containing fuming sulfuric acid as the major portion. A carboxylic acid fluoride $CF_3(CF_2)_3(CH_2CF_2)(CF_2CF_2)CF_2COF$ phase (55.69 g (yield: 72.3%)) was obtained in the upper layer.

Carboxylic acid $CF_3(CF_2)_3(CH_2CF_2)(CF_2CF_2)CF_2COOH$ was quantitatively obtained by adding water to the carboxylic acid fluoride, followed by stirring. The surface tension of the compound was measured at each concentration at ordinary temperature using a maximum bubble pressure method. As a result, the critical micelle concentration [CMC] was 0.51 wt. %, and the surface tension at that time was 20.0 mN/m.

Example 1

2.86 g (6.0 mmol) of $CF_3(CF_2)_3(CH_2CF_2)(CF_2CF_2)CF_2COOH$ was added and dissolved in 25 ml of diethyl ether in a screw tube in which a 50-ml stirrer was equipped. Then, 1.94 g (12.7 mmol) of 1,8-diazabicyclo[5.4.0]undec-7-ene [DBU] was added thereto, and the mixture was stirred at room temperature. The reaction was tracked by 1H-NMR and 19F-NMR, and it was confirmed that almost all of the raw material compounds was consumed after 88 hours. Then, the reaction was terminated.

After 1 M hydrochloric acid was added to the reaction mixture for quenching, washing with water and 1 M hydrochloric acid was performed, and the organic phase was dried over anhydrous magnesium sulfate. The drying agent was filtered off, and the solvent was removed, thereby obtaining 1.32 g (yield: 48%) of brown viscous liquid.

The results of $^1$H-NMR and $^{19}$F-NMR of the mixture revealed that the brown viscous liquid was a mixture of dehydrofluorination products of $CF_3(CF_2)_3(CH_2CF_2)(CF_2CF_2)CF_2COOH$ (n=4, m=1). $CF_3(CF_2)_3CH$=$CF(CF_2CF_2)CF_2COOH$ $CF_3(CF_2)_2CF$=$CHCF_2(CF_2CF_2)CF_2COOH$ $^1$H-NMIR [$(CD_3)_2CO$,TMS]
δ(ppm): 6.88($CF_3CF_2CF_2CF_2\underline{CH}$=$CFCF_2CF_2CF_2COOH$) ($CF_3CF_2CF_2CF$=$\underline{CH}CF_2CF_2CF_2COOH$)

$^{19}$F-NMR [$(CD_3)_2CO,C_6F_6$]
δ(ppm): −126.8($CF_3\underline{CF_2}CF_2CF$=$CHCF_2CF_2CF_2COOH$)
−124.9($CF_3\underline{CF_2}CF_2CF_2CH$=$CFCF_2CF_2CF_2COOH$)
−123.3($CF_3CF_2\underline{CF_2}CF_2CH$=$CFCF_2\underline{CF_2}CF_2COOH$)
−122.6($CF_3CF_2CF_2CF$=$CHCF_2\underline{CF_2}CF_2CF_2COOH$)
−121.6($CF_3CF_2\underline{CF_2}CF$=$CHCF_2CF_2CF_2CF_2COOH$)
−118.4($CF_3CF_2CF_2CF$=$CHCF_2CF_2CF_2CF_2COOH$)
−117.9($CF_3CF_2CF_2CF$=$CHCF_2CF_2CF_2\underline{CF_2}COOH$)
−117.7($CF_3CF_2CF_2CF_2CH$=$CFCF_2CF_2\underline{CF_2}COOH$)
−117.3($CF_3CF_2CF_2CF_2CH$=$CF\underline{CF_2}CF_2CF_2COOH$)
−111.5($CF_3CF_2CF_2\underline{CF}$=$CHCF_2CF_2CF_2CF_2COOH$)
−109.9($CF_3CF_2CF_2CF_2CH$=$CF\underline{CF_2}CF_2CF_2COOH$)
−108.4($CF_3CF_2CF_2\underline{CF_2}CH$=$CFCF_2CF_2CF_2COOH$)
($CF_3CF_2CF_2CF$=$CH\underline{CF_2}CF_2CF_2CF_2COOH$)
−80.2($\underline{CF_3}CF_2CF_2CF_2CH$=$CFCF_2CF_2CF_2COOH$)
−79.9($\underline{CF_3}CF_2CF_2CF$=$CHCF_2CF_2CF_2CF_2COOH$)

Example 2

1.4 wt. % of aqueous ammonia was added to the dehydrofluorinated carboxylic acid mixture obtained in Example 1, and the resulting mixture was stirred, thereby quantitatively obtaining a carboxylic acid ammonium salts mixture.

$CF_3(CF_2)_3CH$=$CF(CF_2CF_2)CF_2COONH_4$ $CF_3(CF_2)_2CF$=$CHCF_2(CF_2CF_2)CF_2COONH_4$

The surface tension of the carboxylic acid ammonium salts mixture was measured at each concentration at ordinary temperature using a maximum bubble pressure method. As a result, the critical micelle concentration [CMC] was 0.31 wt. %, and the surface tension at that time was 18.2 mN/m.

These values are better than the measurement results of perfluorooctanoic acid ammonium under the same conditions (CMC: 0.48 wt. %, surface tension: 20.0 mN/m).

Comparative Example 1

In Example 1, the reaction was performed using 0.71 g (12.7 mmol) of KOH in place of DBU, and 40 ml of methanol in place of diethyl ether. As a result, complicated side reactions occurred in the terminal carboxylic acid moiety, and the dehydrofluorination products shown in Example 1 were not obtained.

Comparative Example 2

In Example 1, the reaction was performed under reflux conditions for 96 hours using 1.21 g (4.0 mmol) of triethylamine in place of DBU; however, the reaction did not proceed, and the dehydrofluorination products shown in Example 1 were not obtained.

Example 3

The following components were charged in a stainless steel pressure reactor having a capacity of 10 L and equipped with a stirrer.

| | |
|---|---|
| Carboxylic acid ammonium salts mixture obtained in Example 2 | 20 g |
| $Na_2HPO_4 \cdot 12H_2O$ (buffer) | 20 g |
| Ethyl malonate (chain transfer agent) | 2.6 g |
| Ion exchanged water | 5,100 g |

Nitrogen substitution was performed to remove oxygen from the reactor. Thereafter, 120 g of hexafluoropropylene [HFP] and 351 g of a vinylidene fluoride [VdF]/tetrafluoroethylene [TFE] mixed gas (VdF/TFE molar ratio: 57.8/42.2) were introduced, and the internal temperature of the reactor was raised to 80° C. The internal pressure of the reactor when the temperature reached 80° C. was 2.14 MPa·G.

After the stability of the internal temperature of the reactor was confirmed, 100 g of aqueous solution in which 0.48 g of ammonium persulfate was dissolved was introduced into the reactor as a polymerization initiator, and the polymerization reaction was initiated. When the polymerization reaction proceeded and the internal pressure of the reactor reached 1.75 MPa·G, a VdF/TFE/HFP (molar ratio: 54.4/39.7/5.9) mixed gas was introduced, and the pressure was raised to 1.85 MPa·G. During the polymerization reaction, the three-component mixed gas having this composition was introduced to thereby maintain the reaction pressure in a range of 1.75 to 1.85 MPa·G.

When the total amount of the three-component mixed gas added in batches reached 1,680 g, the introduction of the mixed gas was stopped. When the internal pressure of the reactor reached 1.75 MPa·G, the reactor was cooled to terminate the polymerization reaction. It took 240 minutes from the supply of the polymerization initiator to the termination of the polymerization reaction, and 6,400 g of fluorine-containing polymer latex was obtained.

The obtained fluorine-containing polymer latex was placed in the same amount of 1 wt. % $CaCl_2$ aqueous solution, and the latex was coagulated by salting out. Then, filtration, washing 5 times with 5-fold amount of ion exchanged water, and vacuum drying were performed, and 1,540 g of resin-like VdF/TFE/HFP terpolymer copolymer was obtained.

The copolymerization composition (measured by $^{19}$F-NMR) of the resin-like terpolymer was VdF/TFE/HFP=55.1/40.8/4.1 (molar ratio), and the weight average molecular weight Mw (measured by GPC) thereof was about $5.8\times10^5$.

Moreover, the amount of the emulsifying agent remaining in the terpolymer was measured in the following manner.

The emulsifying agent in the terpolymer powder was soxhlet-extracted with an ethanol/water (volume ratio: 95/5) mixed solution, and the obtained extract was measured by LC-MS/MS under the following conditions. As a result, the amount of the remaining emulsifying agent was 17.0 ppm.

LC-MS/MS measurement: using a system comprising the LC-20A prominence series (produced by Shimadzu Corporation) and 4000Q TRAP (produced by Applied Biosystems Japan)

Column: using Mightysil RP-18(L) GP100-20 (5 µm, produced by Kanto Chemical Co., Inc.)

Mobile phase: using gradient of two solutions: (A) 5 mmol/L ammonium acetate aqueous solution and (B) acetonitrile Further, in order to evaluate the stability of the fluorine-containing polymer latex, the amount of aggregates (PHL) in the latex after the polymerization reaction was measured. The measurement was performed by filtering about 1 kg of latex through a 300-mesh filter, and measuring the filtration residue. PHL was calculated by the following formula, and a value of 0.0034 PHL was obtained.

PHL=filtration residue (g)×100/amount of filtration latex (g)

The invention claimed is:

1. A mixture of polyfluoroalkene carboxylic acids or salts thereof corresponding to the general formulas:

and

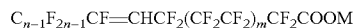

wherein M is a hydrogen atom, an ammonium salt, an organic amine salt or an alkali metal, n is an integer of 1 to 6 and m is an integer of 0 to 2.

2. A process for producing a mixture of polyfluoroalkene carboxylic acids corresponding to the general formulas:

and

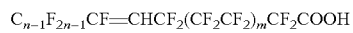

wherein n is an integer of 1 to 6 and m is an integer of 0 to 2, which comprises subjecting a polyfluoroalkane carboxylic acids corresponding to the general formula:

wherein n is an integer of 1 to 6 and m is an integer of 0 to 2, to a dehydrofluorination reaction in the presence of a nitrogen-containing heterocyclic compound catalyst, wherein the nitrogen-containing heterocyclic compound used as a catalyst is 1,8-diazabicyclo[5.4.0]undec-7-ene or 1,5-diazabicyclo[4.3.0]non-5-ene.

3. A process for producing a mixture of polyfluoroalkene carboxylic acid salts, which comprises reacting a mixture of polyfluoroalkene carboxylic acids obtained by the production process according to claim 2 with an ammonia, an organic amine or an alkali metal hydroxide.

4. In a process for conducting a polymerization reaction of fluorine-containing monomer the improvement comprising contacting a mixture of polyfluoroalkene carboxylic acids or salts thereof according to claim 1, as an emulsifying agent, with a polymerization mixture.

5. In a process for conducting a polymerization reaction of fluorine-containing monomer the improvement comprising contacting a mixture of polyfluoroalkene carboxylic acids or salts thereof according to claim 1, as an emulsifying agent and/or a dispersing agent, with a polymerization mixture.

* * * * *